(12) United States Patent
Panzera

(10) Patent No.: US 7,943,068 B2
(45) Date of Patent: May 17, 2011

(54) METHOD OF MAKING A DENTAL RESTORATION

(75) Inventor: Carlino Panzera, Hillsborough, NJ (US)

(73) Assignee: Ivoclar Vivadent, Inc., Amherst, NY (US)

( * ) Notice: Subject to any disclaimer, the term of this patent is extended or adjusted under 35 U.S.C. 154(b) by 216 days.

(21) Appl. No.: 11/598,085

(22) Filed: Nov. 13, 2006

(65) Prior Publication Data

US 2007/0056467 A1 Mar. 15, 2007

Related U.S. Application Data

(62) Division of application No. 10/693,731, filed on Oct. 24, 2003, now abandoned, which is a division of application No. 09/905,806, filed on Jul. 13, 2001, now Pat. No. 6,689,202.

(60) Provisional application No. 60/219,893, filed on Jul. 21, 2000.

(51) Int. Cl.
*A61C 13/00* (2006.01)
*A61C 13/20* (2006.01)

(52) U.S. Cl. .............. 264/16; 264/19; 264/643; 106/35

(58) Field of Classification Search .................... 264/16, 264/19, 20, 643
See application file for complete search history.

(56) References Cited

U.S. PATENT DOCUMENTS

| | | | | |
|---|---|---|---|---|
| 3,470,615 | A * | 10/1969 | Petner | 433/223 |
| 3,502,466 | A * | 3/1970 | Vickery | |
| 4,369,068 | A * | 1/1983 | Hausselt et al. | |
| 4,459,112 | A * | 7/1984 | Shoher et al. | 433/222.1 |
| 4,575,805 | A * | 3/1986 | Moermann et al. | |
| 4,663,720 | A * | 5/1987 | Duret et al. | |
| 4,689,197 | A * | 8/1987 | Groll et al. | |
| 4,717,341 | A * | 1/1988 | Goldberg et al. | |
| 4,766,704 | A * | 8/1988 | Brandestini et al. | |
| 4,772,436 | A * | 9/1988 | Tyszblat | |
| 4,828,495 | A * | 5/1989 | Bell et al. | |
| 4,894,012 | A * | 1/1990 | Goldberg et al. | |
| 4,937,928 | A * | 7/1990 | Van der Zel | |
| 4,980,124 | A * | 12/1990 | Dimmer | |
| 5,062,798 | A * | 11/1991 | Tsuge et al. | |
| 5,121,334 | A * | 6/1992 | Riley et al. | 700/163 |
| 5,304,239 | A * | 4/1994 | Schwabe et al. | |
| 5,336,091 | A * | 8/1994 | Shoher et al. | 433/215 |
| 5,342,201 | A * | 8/1994 | Oden | |
| 5,378,154 | A * | 1/1995 | Van der Zel | |
| 5,452,219 | A * | 9/1995 | Dehoff et al. | |
| 5,507,981 | A * | 4/1996 | Petticrew | |
| 5,653,791 | A * | 8/1997 | Panzera et al. | |
| 5,775,912 | A * | 7/1998 | Panzera et al. | 433/223 |
| 5,910,273 | A * | 6/1999 | Thiel et al. | |
| 5,944,884 | A * | 8/1999 | Panzera et al. | |
| 5,968,856 | A * | 10/1999 | Schweiger et al. | |
| 6,028,672 | A * | 2/2000 | Geng | |
| 6,186,790 | B1 * | 2/2001 | Karmaker et al. | |
| 6,200,136 | B1 * | 3/2001 | Prasad et al. | |
| 6,455,451 | B1 * | 9/2002 | Brodkin et al. | |
| 6,517,623 | B1 * | 2/2003 | Brodkin et al. | |
| 6,613,273 | B2 * | 9/2003 | Daskalon et al. | |

FOREIGN PATENT DOCUMENTS

| | | | |
|---|---|---|---|
| EP | 0 523 019 A2 | * | 1/1993 |
| IT | 94A000003 | * | 12/1994 |
| WO | 97/30654 | * | 8/1997 |
| WO | 01/13814 A1 | * | 3/2001 |
| WO | 01/15620 A1 | * | 3/2001 |
| WO | 02/22041 | * | 3/2002 |

OTHER PUBLICATIONS

Sadoun, M., and S. Perelmuter, Alumina-Zirconia Machinable Abutments for Imiplant-Supported Single Tooth Anterior Crowns, Practical Periodontics and Aesthetic Dentistry, vol. 9, No. 9 (1997), pp. 1047-1054.*

Kawai, C., and Ak. Yamakawa, Effect of Porosity and Microstructure on the Strength of Si3N4: Designed Microstructure for High Strength, High Thermal Shock Resistance, and Facile Machining, J. Am. Ceram. Soc., vol. 80, No. 10 (1997), pp. 2705-2708.*

Suganuma, K., et al., Mechanical properties and microstructures of machinable silicon carbide, J. of Materials Science, vol. 28 (1993), pp. 1175-1181.*

Wen et al., "Effects of Sintering Temperature Calefactive Velocity on the Partially Sintered Alumina Block for Dental CAD/CAM", Abstract, *Disi Junyi Daxue Xuebao* (2001), 2(1), pp. 913-915.

Jeneric/Pentron, Inc., *SinterKor Instruction Manual*, Rev. 3.1, Jul. 2000.

Wolf et al., "Mechanical Properties and Failure Analysis of Alumina Glass Dental Composites", (Abstract), *Journal of American Ceramic Society* (1996), 79(7), pp. 1769-1776.

Wolf et al., "Colloidal and Thermal Processing Variables for Alumina Glass Dental Composites", (Abstract), *Ceramic Transactions* (1995), 48, pp. 261-267.

(Continued)

*Primary Examiner* — Monica A Huson
(74) *Attorney, Agent, or Firm* — Ann M. Knab

(57) ABSTRACT

Blocks of material are prepared in a variety of shapes and sizes to be used in the fabrication of models for dental restorations. The material comprises a partially sintered ceramic material. The blocks are used to manufacture molds using CAD/CAM methods and equipment. The molds are useful in the manufacture of dental restorations using ceramics, metals, alloys, or powders thereof, and composite materials. The models milled from the blanks may be used to manufacture a variety of dental restorations including, but not limited to, crowns, bridges, space maintainers, tooth replacement appliances, orthodontic retainers, dentures, posts, jackets, inlays, onlays, facings, veneers, facets, implants, abutments, splints, partial crowns, teeth, cylinders, pins, and connectors.

17 Claims, No Drawings

OTHER PUBLICATIONS

Luo et al., "Research on Bending Strength and Fracture Toughness of Alumina Glass Composites", (Abstract), *Huaxi Yike Daxue Xuebao* (1998), 29(4), pp. 383-386.

Luo et al., "Development of Partially Sintered Alumina Block for Dental CAD/CAM and Mechanical Properties Testing", (Abstract), *Zhonghua Kouqiang Yixue Zazhi* (1999), 34(4), pp. 202-204.

Luo et al., "Strength and Fracture Toughness of MgO-Modified Glass Infiltrated Alumina for CAD/CAM", (Abstract), *Dental Materials* (2002), 18(3), pp. 216-220.

Hooker et al., "Properties of Rare Earth Oxide Doped Translucent Polycrystalline Alumina", (Abstract), *Journal of Materials Processing Technology* (2001), 118 (1-3), pp. 256-260.

Zhang et al., "Mechanical Properties and Microstructure of Alumina-Glass Dental Composites", (Abstract), *Proceedings of the China International Conference on High-Performance Ceramics*, 1st, Beijing, China, Oct. 31-Nov. 3, 1998, Meeting Date 1998, pp. 471-474.

S. C. Nanjangud et al., "Mechanical Behavior of Porous Glasses produced by Sintering of Spherical Particles", *Journal of the European Chemical Society*, vol. 15 (1995), pp. 655-660.

D. Hardy et al., "Mechanical Properties of a Partially Sintered Alumina", *Journal of the European Ceramic Society*, vol. 15 (1995), pp. 769-775.

* cited by examiner

METHOD OF MAKING A DENTAL RESTORATION

CROSS-REFERENCE TO RELATED APPLICATIONS

This is application claims priority to U.S. Provisional Application No. 60/219,893 filed Jul. 21, 2000 which is incorporated herein by reference.

FIELD OF THE INVENTION

The present invention relates generally to molds for and methods of manufacturing dental restorations and more specifically to molds for and methods of manufacturing dental restorations using CAD/CAM methods.

BACKGROUND OF THE INVENTION

In the manufacture of dental restorations, the dental practitioner prepares the tooth to be restored by grinding the subject tooth or teeth down to form one or more tooth preparations to which the prosthetic device is to be attached. An impression of the tooth preparation is taken in an elastic material and the impression is used to produce a model with dies. The model or die is then used to prepare the restoration thereon such as by casting or pressing a material onto the die.

U.S. Pat. No. 4,937,928, which is hereby incorporated by reference, is directed to a method of making a dental restoration wherein a model of a dental preparation is made by milling a refractory material under the control of a CAD/CAM system. The refractory material is a high strength material such as magnesia, which is needed to withstand the high temperatures used to process the dental materials used therein, e.g., palladium which has a melting temperature of 1552° C. Due to the high strength of the refractory material, it may be difficult to mill the material into the desired shape. Moreover, the milling tools become quickly worn and must be replaced frequently leading to high costs of production. Furthermore, magnesia is known to be unstable. It is hydroscopic and tends to absorb and react easily with moisture. Depending upon the high reactivity of magnesia, there is no guarantee that it will sinter consistently every time. The dimensions may change during sintering, resulting in a restoration which does not fit the tooth properly.

There is a need to provide a softer material for producing models and dies for the manufacture of dental restorations. It is desirable that the soft material be stable and exhibit good thermal properties. It is beneficial that the soft material be strong to withstand high temperature and pressing operations.

SUMMARY OF THE INVENTION

These and other objects and advantages are accomplished by blocks or blanks of material prepared in a variety of shapes and sizes to be used in the fabrication of models for dental restorations. The blanks may be provided in a variety of shapes including but not limited to square, circular, rectangular, cylindrical and triangular shapes. The material comprises a partially sintered ceramic material. The blanks are used to manufacture molds using CAD/CAM methods and equipment. The molds are useful in the manufacture of dental restorations using ceramics, metals, alloys, or powders thereof, and composite materials. The models milled from the blanks may be used to manufacture a variety of dental restorations including, but not limited to, crowns, bridges, space maintainers, tooth replacement appliances, orthodontic retainers, dentures, posts, jackets, inlays, onlays, facings, veneers, facets, implants, abutments, splints, partial crowns, teeth, cylinders, pins, and connectors.

DETAILED DESCRIPTION OF THE INVENTION

As will be appreciated, the present invention provides materials and methods of manufacturing dental restorations using blocks or blanks of material prepared in a variety of shapes and sizes to be used in the fabrication of dental restorations. The material may comprise any partially sintered ceramic material, i.e., a partially sintered material is a material that is not sintered to full density, making it easy to machine. Useful partially sintered ceramic materials are refractory, not reactive, and essentially inert during subsequent firing steps. Sinterable refractory ceramic materials thus include but are not limited to quartz cristobalite, other forms of silica, leucite, various forms of zirconia, hafnia, zircon, alumina, magnesia, zircon, aluminosilicate, cordierite, mica, silicon nitride, silicon carbide, silica-alumina-nitrides, mullite, various garnets, or mixtures thereof.

It is often useful to formulate the refractory ceramic materials with a binder, which may be either organic or inorganic. Organic binders are well known, for example, polyvinyl pyrrolidine, polyvinyl alcohol, polyvinyl acetate, polyvinyl chloride, polyvinyl butryal and polystyrene, and mixtures thereof. Inorganic binders are known and may include but are not limited to magnesium oxide, ammonium phosphate, colloidal silica, calcium sulfate (gypsum), ethyl silicate, silica, magnesium phosphate, silica compounds such as alkaline silicates and silica hydrosol, colloidal clays, and mixtures thereof.

In general, such ceramics when partially sintered as used herein are sintered to less than about 92%, more preferably less than about 80%, even more preferably less than about 75% of theoretical full density.

Castable refractory materials and investment refractory materials are particularly useful in the formation of partially sintered ceramic materials. Investment refractory materials useful herein include gypsum-bonded, phosphate-bonded and ethyl silicate-bonded investment materials. These investment materials normally contain up to about 80% of a refractory material such as quartz, cristobolite, other forms of silica, leucite, various forms of zirconia, hafnia, zircon, etc. or mixtures thereof. These investment materials are commercially available and are widely used in dental laboratories for various purposes, one such purpose being for creation of a mold space during the "lost wax process." Examples of commercially available investment materials include RapidVest® investment available from Jeneric®/Pentron® Inc., Wallingford, Ct.; Accu-Press™ investment available from Talladium Inc., Valencia, Calif.; PC15™ investment available from WhipMix Corporation, Louisville, Ky.; and Speed™ investment available from Ivo clar North America, Amherst, N.Y. Examples of castable refractory materials include Ceramacast™ brand castable refractory materials from Aremco Products Inc. (Ossining, N.Y.). Ceramacast™ castables comprise a mixture of a filler and a bonding agent whereby the filler is based on alumina, zirconia, magnesia, zircon, aluminosilicate, cordierite, mica, and mixtures thereof.

The blanks may be fabricated by known casting methods. Such methods will, of course, depend on the particular ceramic material and optional binder, and are well-known to one of ordinary skill in the art or may be determined through routine experimentation. The methods and materials for mass production of the blanks herein described include but are not limited to mass-production processes such as casting, slip-casting, extrusion and dry-pressing.

The partially sintered ceramic material used to make the blanks exhibits a flexural strength in the range from about 1 to about 75 MPa and preferably in the range from about 3 to about 20 MPa.

It is important that the thermal expansion of the mold and the thermal expansion of the material applied to the mold be compatible to prevent weakening or cracking of the dental restoration. It is preferable that the mold have a thermal expansion that is lower than the thermal expansion of the material applied thereto (ceramic, metal, alloy, composite), although depending upon the materials used, the thermal expansion of the material applied may be lower than that of the mold. It should be mentioned that the materials used to fabricate the mold are stable and fire consistently so that there is little or no chance that the dimensions of the mold will change during the subsequent firing steps.

The blanks are used to manufacture molds using CAD/CAM methods and equipment. The process may include the steps of obtaining data regarding the patient's tooth or teeth to be restored in order to machine or mill a mold which replicates the tooth or teeth to be restored. This may be performed by known processes such as by photographing the patient's tooth or scanning the patient's tooth, such as by a digital or optical device. Alternatively, conventional methods may be used whereby an impression is taken of the patient's mouth and data is obtained from the impression or from the mold made from the impression. The data received is used to mill a mold from the soft-sintered ceramic material. Examples of CAD/CAM methods and equipment are described in U.S. Pat. Nos. 4,937,928, 5,910,273, 4,575,805, and 4,663,720 and are hereby incorporated by reference. Examples of commercially available CAD/CAM systems include the Cerec™ system available from Sirona™ USA, Charlotte, N.C., and the Pro 50™ system available from Cynovad™, Quebec City, Canada.

The molds or dies obtained are used in manufacturing dental restorations such as those described in U.S. Pat. Nos. 4,689,197, 4,828,495, 4,980,124, 3,502,466, 4,369,068, 5,653,791, and 5,944,884 and copending, commonly owned U.S. patent application Ser. No. 09/757,916, filed Jan. 10, 2001, copending, commonly owned U.S. patent application Ser. No. 09/653,377, filed Sep. 1, 2000, which are all hereby incorporated by reference.

The molds are useful in the manufacture of dental restorations using ceramics, metals, alloys, or powders thereof, and composite materials.

Ceramic materials include high strength ceramic materials such as alumina, zirconia, silicon nitride, silicon carbide, silica-alumina-nitrides, mullite, various garnets etc. and porcelain materials such as commercially available OPC® 3G™ porcelain and OPC® porcelain, both available from Jeneric/Pentron Inc., Wallingford, Ct., and commercially available Empress™ porcelain and Empress II™ porcelain, both available from Ivoclar North America, Amherst, Ny.

Processes used in the manufacture of ceramic dental restorations are well known; for example, pressing ceramic materials onto a mold into a space formed by the lost wax process.

Such methods are set forth in U.S. Pat. Nos. 5,968,856, 5,507,981, copending, commonly owned U.S. patent application Ser. No. 09/458,919, filed Dec. 10, 1999, and copending, commonly owned U.S. patent application Ser. No. 09/640,941, filed Aug. 17, 2000, which are all hereby incorporated by reference.

Metals or alloys in the form of foils or in the form of powders in combination with a binder, such as wax, may be used in the form of a paste, tape or a sheet. Examples of such materials include commercially available Captek® materials available from Precious Chemicals Inc., Longwood, Fla., and SinterKor™ materials, available from Jeneric/Pentron Inc., Wallingford, Conn., and also as disclosed in the SinterKor™ Instruction Manual from Jeneric/Pentron, Revision 3.1, 7/2000, which is hereby incorporated by reference for all materials and processes therein. Moreover U.S. patent application Ser. No. 09/757,916, describes methods of manufacture using the aforementioned materials and is hereby incorporated by reference. Accordingly, the paste may be pressed onto and around the die or the sheet or foil may be cut to a desired shape to fit onto the die. The process is continued as described and known to form the desired dental restoration.

Composite materials may include those materials such as those set forth in U.S. Pat. Nos. 4,717,341 and 4,894,012 to Goldberg, U.S. Pat. No. 6,200,136 to Prasad, and U.S. Pat. No. 6,186,790 to Karmaker, all of which are incorporated by reference herein. The composite material may be any known composite material such as a resin or polymeric material combined with particulate and/or fiber material or mixtures thereof. Preferably, the composite is a polymeric material having particulate therein such as commercially available Sculpture® composite available from Jeneric/Pentron Inc., Wallingford, Conn., or polymeric material reinforced with fiber and/or particulate such as commercially available FibreKor® composite from Jeneric/Pentron, Inc., Wallingford, Conn..

One or more layers of material may be further applied to the dental restoration to finish the restoration. Such layers may be fabricated of a porcelain or composite material.

The models milled from the blanks may used to manufacture a variety of dental restorations including, but not limited to, crowns, bridges, space maintainers, tooth replacement appliances, orthodontic retainers, dentures, posts, jackets, inlays, onlays, facings, veneers, facets, implants, abutments, splints, partial crowns, teeth, cylinders, pins, and connectors.

The invention facilitates and eases the manufacture of dental restorations by providing millable, soft blanks of material that can be easily machined into models or dies.

The following examples illustrate the present invention.

EXAMPLE 1

A mixture of quartz powder, magnesium oxide and ammonium phosphate was made into a blank by mixing it with 25% by wt. colloidal silica (40% by wt. concentration) and pouring it into molds. The mixture was allowed to cure for about 15 minutes and sintered to about 1000° C. for 1 hour to effect a "soft sintered" state. The cylinder had dimensions of about 0.5 inches in diameter and about 0.7 inches high. The resultant cylinder was held together, but was not too strong such that it could be easily machined into a tooth shape. The cylinder was machined into a mold and a sheet of Sinterkor™ material was cut and applied onto the mold and thereafter sintered at 1000° C. using Sinterkor™ techniques and processing parameters. The resulting Sinterkor™ restoration was removed from the mold. The mold was inspected and showed no changes or deformation in shape from the originally molded shape.

EXAMPLE 2

A mixture of leucite powder, magnesia and ammonium phosphate was mixed with 25% by wt. colloidal silica (40% by wt concentration) poured into molds, allowed to cure for about 15 minutes and sintered to 1000° C. for one hour to effect a "soft sintered" state. The cylinder had dimensions of about 0.5 inches in diameter and about 0.7 inches high. The resultant cylinder was held together, but was not too strong such that it could be easily machined into a tooth shape. The cylinder was milled into a mold and the mold was used to manufacture a dental crown using OPC® porcelain material. The mold was invested using the lost wax process and a pellet of OPC® porcelain material was pressed onto the mold to form the dental restoration at approximately 910° C. The mold was inspected and showed no changes or deformation in shape from the originally molded shape.

EXAMPLE 3

A mixture of zirconia (stabilized with 4 mole % CaO) 20% by wt. quartz and 3% by wt. of Duramax™ binder, available from Rohm Hass, Philadelphia, Pa., was cold pressed in a steel die, and sintered in air to 1100° C. for one hour to effect a "soft sintered" state. The blank measured 0.5 inches in diameter by 0.75 inches high. The blank was machined into a mold and a sheet of Sinterkor™ material was cut and applied onto the mold and thereafter sintered at 1000° C. using Sinterkor™ techniques and processing parameters. The resultant Sinterkor™ restoration was removed from the mold. The mold was inspected and showed no changes or deformation in shape from the originally molded shape.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method for making a dental restoration comprising:
   milling a dental model from a partially sintered refractory ceramic material, wherein the partially sintered refractory material has a flexural strength in the range from about 1 to about 20 MPa;
   applying dental material thereon;
   curing the dental material on the model to obtain a dental restoration, wherein the model is stable such that there is no change in the dimensions of the model during curing; and
   removing the dental restoration from the model.

2. The method of claim 1 wherein the curing process comprises sintering, light curing or heat curing.

3. The method of claim 1 wherein the dental material comprises a metal material, a ceramic material, a composite material or mixtures thereof.

4. The method of claim 3 wherein the metal material comprises a single metal or an alloy of two or more metals.

5. The method of claim 3 wherein the metal material comprises metal powder in combination with a binder.

6. The method of claim 5 wherein the metal powder in combination with the binder is in the form a sheet.

7. The method of claim 3 wherein the metal material is in the form of a foil.

8. The method of claim 3 wherein the ceramic material comprises porcelain.

9. The method of claim 3 wherein the ceramic comprises a high-strength material comprising alumina, zirconia, silicon nitride, silicon carbide, silica-alumina nitrides, mullite, garnet, or a combination thereof.

10. The method of claim 3 wherein the composite material comprises a material selected from a particulate-reinforced polymeric material, a fiber-reinforced polymeric material and mixtures thereof.

11. The method of claim 1 wherein one or more layers of material are applied on the dental restoration.

12. The method of claim 11 wherein the one or more layers of material comprises a material selected from the group consisting of a porcelain or composite material.

13. A method for making a dental restoration comprising:
   obtaining data of a patient's tooth;
   milling a dental model from a partially sintered refractory ceramic material based on the data obtained from the patient's tooth, wherein the partially sintered refractory material has a flexural strength in the range from about 1 to about 20 MPa;
   applying dental material onto the model;
   heating the model and dental material thereon to obtain a dental restoration, wherein the model is stable such that there is no change in the dimensions of the model during heating; and
   removing the dental restoration from the model.

14. The method of claim 13 wherein the data obtained from the patient's tooth is acquired by photographing the patient's tooth.

15. The method of claim 13 wherein the data obtained from the patient's tooth is acquired by scanning the patient's tooth.

16. The method of claim 1 wherein the refractory material comprises one or more materials selected from the group consisting of alumina, zirconia, magnesia, zircon, aluminosilicate, cordierite, mica, quartz, cristobolite, silica, silicon nitride, silicon carbide, leucite, silica-alumina-nitrides, mullite, garnet, or mixtures thereof.

17. The method of claim 13 wherein the refractory material comprises one or more materials selected from the group consisting of alumina, zirconia, magnesia, zircon, aluminosilicate, cordierite, mica, quartz, cristobolite, silica, silicon nitride, silicon carbide, leucite, silica-alumina-nitrides, mullite, garnet, or mixtures thereof.

* * * * *